(12) United States Patent
Kritzler

(10) Patent No.: US 6,699,331 B1
(45) Date of Patent: Mar. 2, 2004

(54) ENDOSCOPE CLEANING DEVICE

(75) Inventor: Steven Kritzler, Rosebery (AU)

(73) Assignee: Novapharm Research (Australia) PTY LTD, NSW (AU)

(*) Notice: Subject to any disclaimer, the term of this patent is extended or adjusted under 35 U.S.C. 154(b) by 0 days.

(21) Appl. No.: 09/763,133

(22) PCT Filed: Aug. 19, 1999

(86) PCT No.: PCT/AU99/00669
§ 371 (c)(1),
(2), (4) Date: Jun. 12, 2001

(87) PCT Pub. No.: WO00/10476
PCT Pub. Date: Mar. 2, 2000

(30) Foreign Application Priority Data

Aug. 20, 1998 (AU) .................................................. PP5370

(51) Int. Cl.$^7$ ................................................. B08B 9/04
(52) U.S. Cl. ................ 134/8; 134/22.11; 134/22.14; 15/104.05; 15/104.16
(58) Field of Search ................ 134/8, 22.1, 22.12, 134/22.13, 22.14; 15/104.05, 104.16

(56) References Cited

U.S. PATENT DOCUMENTS

| | | | | |
|---|---|---|---|---|
| 363,951 A | * | 5/1887 | Forster | 15/104.16 |
| 387,410 A | * | 8/1888 | Gillette | 15/104.16 |
| 449,080 A | * | 3/1891 | Mackay | 15/104.16 |
| 4,715,747 A | * | 12/1987 | Behrens | 405/303 |
| 4,873,778 A | | 10/1989 | Stipp | 42/95 |
| 4,962,607 A | | 10/1990 | Baldwin | 42/95 |
| 5,555,588 A | * | 9/1996 | Viesehon | 15/104.16 |
| 5,814,160 A | * | 9/1998 | Orlando | 134/8 |
| 5,840,251 A | * | 11/1998 | Iwaki | 422/36 |
| 5,964,004 A | * | 10/1999 | Bean | 15/104.16 |
| 6,045,623 A | * | 4/2000 | Cannon | 134/8 |

FOREIGN PATENT DOCUMENTS

| | | |
|---|---|---|
| AU | 39216/97 | 2/1998 |
| JP | 8-173379 | 7/1996 |

* cited by examiner

Primary Examiner—Randy Gulakowski
Assistant Examiner—Saeed Chaudhry
(74) Attorney, Agent, or Firm—Leydig, Voit & Mayer, Ltd.

(57) ABSTRACT

Apparatus for wiping a contaminated lumen of an endoscope including a cleaning member having at least one radially extending fin for passing axially through the lumen with at most a small clearance whereby contamination remaining after passage of the member through the lumen is substantially uniformly distributed as a thin film on an internal wall of the lumen. The invention also relates to a method for cleaning a contaminated lumen of an endoscope including pulling or pushing a cleaning member axially through the lumen and treating the uniformly distributed film with a cleaning composition.

37 Claims, 3 Drawing Sheets

ENDOSCOPE CLEANING DEVICE

TECHNICAL FIELD

The present invention relates to cleaning devices and methods, in particular devices and methods for cleaning the interior cavities of contaminated surgical and diagnostic instruments.

The invention has been developed primarily for use in cleaning endoscopes and will be described hereinafter to reference to this application. However, it will be appreciated that the invention is not limited to this particular field of use.

BACKGROUND ART

An endoscope is an elongate cylindrical instrument that may be rigid or flexible and which incorporates an optical, or video, system and a light source. The endoscope is configured such that one end can be inserted to some depth into a surgical incision or body cavity so surfaces at or near the internally inserted end of the endoscope can be viewed by an external observer.

For example, at present, the longest commonly used endoscope is a flexible endoscope called a colonoscope. A colonoscope is used for diagnostic and surgical procedures of the human colon. The colon insertion portion of the instrument is approximately 2 metres long and has one or more hollow channels, or lumens. These lumens are typically 2–4 mm in diameter and run the length of the endoscope. They allow for gas to be injected into the colon to inflate the organ or enable liquids to be sucked out. Additionally, long flexible instruments can be inserted down these or other lumens to allow biopsies to be taken and the wound to be cauterised. These biopsy samples are then drawn back through the lumen and sent for pathology testing.

New endoscopes can achieve exceptional results in performing a variety of surgical procedures whereby very small (2 cm) incisions are all that is required, rather than the previous procedures which required incisions of over 20 cm in length. Furthermore, endoscopic procedures usually enable patients to leave hospital after two or three days rather than the previously necessary 7 to 10 days. Overall, trauma is dramatically reduced.

However, a problem inherent with endoscopes is the contamination of the lumen with biological material from the patient, for example, mucous, saliva, faeces, blood, pieces of tissue etc.

While endoscopes have developed greatly in recent times, most, of the developments have concentrated on technical aspects such as the use of optical fibres and lenses, electronic controls and other engineering features. Progress in the cleaning and disinfection of endoscopes has largely not kept pace with the engineering and electronics developments. More recently very sophisticated chemical and biochemical products have been developed, for example, multi-enzyme detergents which digest all human secretions which may be on endoscope surfaces in order to pre-clean instruments before they are disinfected. Also relatively recently new sterilising-systems using hydrogen peroxide plasma or peracetic acid at elevated temperature have become available.

All soiled endoscopes require thorough and efficient cleaning (known as "pre cleaning") prior to disinfection or sterilisation. Disinfection or sterilisation of an instrument which has not been completely cleaned is impossible and leads to patient infections.

The current procedure for cleaning an endoscope entails the following steps.

1. Removal of the soiled endoscope from the patient.
2. Rinsing the soiled instrument in a sink with a copious amount of water and wiping down the outer sheath with a single use paper or non-woven fabric wipe.
3. Rinsing the endoscope lumens with water using a large syringe or other water jet.
4. Brushing the lumens with an endoscope cleaning brush whilst the instrument is immersed in water.
5. Digestion of the contaminants by immersing the instrument in a multi-enzyme detergent bath. In some places detergent is used rather than enzymes.
6. Rinsing the instrument and the hollow channels with water and then air blowing to substantially dry the surfaces in order to avoid dilution of disinfectants.

The endoscope is then ready for disinfection or sterilisation.

In some variations of the procedure, step 4 and 5 are replaced by a step of brushing while the endoscope is immersed in an enzyme detergent bath.

Typically, the endoscope cleaning brush referred to above has a long flexible stainless steel body composed of a flexible stainless steel wire core covered by tightly coiled flexible stainless-steel. The diameter of this body section is approximately 1 mm. At the end of the body is a 30 mm section of nylon bristles. These flexible bristles are usually interwoven with the stainless steel coils. The bristle section is approximately 5 to 6 mm in diameter. The cleaning brush is used to briskly brush backwards and forward along the whole length of the lumen of the endoscope to remove the maximum amount of biological matter contamination prior to enzyme digestion.

Typically, cleaning brushes used for endoscope cleaning receive a clean and disinfection between each cycle of use, in that they are given a water rinse soaked in an enzyme bath, and usually receive the same disinfection as the endoscope itself. There are no limits on the number of cycles of use of such cleaning brushes and many remain in use after most or at least a significant number of bristles have broken away.

Some procedures, for example diagnostic examination of the human oesophagus and stomach can be accomplished in 10–15 minutes after the patient is sedated, while cleaning and disinfecting, would require over 30 minutes.

Endoscopes are expensive instruments, many costing up to between $20,000–$50,000. Because of this high price, practitioners tend to purchase only the minimum number of instruments necessary to ensure a smooth work flow. As a result, there is considerable pressure to disinfect the endoscope for only the shortest effective time. Any improvement in the time required to disinfect the endoscopes has the potential to reduce the number of instruments which a practitioner needs to purchase.

It is an object of the present invention to provide a device and method to improve the speed and/or efficiency of cleaning endoscopes and the like.

DESCRIPTION OF THE INVENTION

According to a first aspect the invention consists in apparatus for use in cleaning a contaminated lumen of an endoscope, said apparatus comprising a wiping member adapted to pass axially through the lumen with at most a small clearance, whereby contamination, if any, remaining after passage of the member through the lumen is substantially uniformly distributed about the interior of the lumen as a thin film.

For preference the wiping member is attachable, or more preferably permanently attached to an elongate shaft or cable. This may be flexible for flexible endoscopes or rigid for rigid endoscopes. The member may include wiping elements which are, for example, a disk disposed orthogonally to the shaft or it may be a cylinder, sphere, cone, spiral or the like. It is preferred to use one or more disk-shaped fins as wiping elements as these provide a more effective scraping action.

Wiping members which are not fully circumferential at their trailing member leave ridges of contaminant when pulled through the endoscope. The number of ridges will depend upon the design. Even if a number of partially circumferential segments occlude one another to present a full circumference when viewed end on, the trailing member will leave ridges in the contaminant film where the edge of the partially circumferential segment is drawn through the contaminant.

In a particularly preferred embodiment, the wiping member includes approximately 50 circular segments of similar size in close proximity and disposed at 90° to the shaft.

According to a second aspect the invention consists in a method for cleaning a contaminated lumen of an endoscope comprising the steps of:

Pulling or pushing a wiping member axially through the lumen, the wiping member being adapted to wipe the internal wall of the lumen or to pass through with a small clearance whereby remaining contaminants, if any, after passage of the member are uniformly distributed about the interior wall of the lumen as a thin film; and treating the uniform film with a cleaning composition.

In the use of the method, the cleaning composition preferably includes one or more enzymes.

Experiments have been conducted by the present inventor using a transparent tube of the same diameter as an endoscope lumen contaminated with compositions similar to those encountered in use and using the prior art cleaning method. This has revealed that the nature of the bristles mainly serve to move the viscous liquid with its suspended particular matter backwards and forwards rather than to remove it from the hollow tube. The thick viscous, non flowing biological material is simply redispersed in an uneven fashion throughout the lumen, creating in places thick deposits or "ridges" of biological materials that may not be fully digested by the enzymes in the short period of the cleaning phase or are digested more slowly than thinner film sections in the "valleys" between ridges.

The resulting uneven distribution of the contamination increases the overall cleaning time. The thickness of the deposits is a rate determining factor in the enzyme digestion step.

The inventor has found that by use of the present method a much greater proportion of contaminant can be removed in a single pass through the lumen and any remaining contaminant is spread much more uniformly and as a thin film which is rapidly and uniformly attacked during the digestion step.

According to a third aspect the invention consists in a method for manufacture of an endoscope cleaning apparatus comprising the step of moulding a wiping member comprising one or more radially directed fins in situ on an elongated shaft or cable.

The wiping member may be formed integrally with the shaft, or may be made separately. It may have a solid core or a hollow core.

The invention will now be more particularly described by way of example only with reference to the accompanying drawings.

BEST MODE FOR CARRYING OUT THE INVENTION

Figure 1:
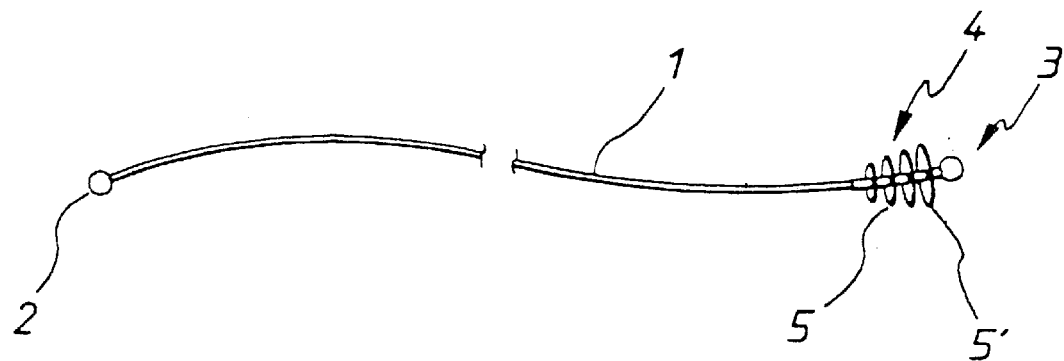
FIG. 1 shows a preferred embodiment of an apparatus for use in cleaning a contaminated lumen of an endoscope in accordance with the present invention.
Figure 2:
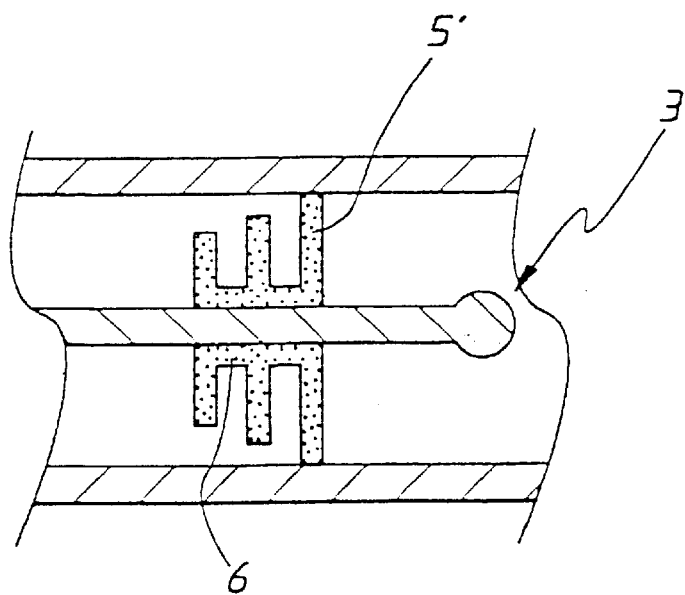
FIG. 2 shows a cross section of the preferred embodiment when inserted into the lumen of an endoscope.

A preferred embodiment of the invention has a long slender body 1 composed of a flexible material having a pulling end 2 and defining a pulling direction. At or adjacent the other end 3 is an apparatus 4 comprising a plurality of wiping members 5 which in the present example consists of axially spaced apart disk shaped fins increasing in diameter in a direction opposite the pulling direction. The maximum diameter of disk 5' is very marginally less than the diameter of the lumen. The disks extend radially from a solid flexible core 6 which is a tight fit coaxially on body 1. The end 3 is press formed so as to retain the fins. The other end of the body 3 is preferably rounded so as not to damage the interior surface of the lumen. Body 1 has a length at least 20–30 mm greater than the length of the hollow channel. The round ended body of the device is inserted into the proximal end of the hollow channel and pushed down until it emerges from the distal end whereupon it is grasped and pulled through, removing the bulk of the contamination. Ideally, this procedure does not require repetition. All residual biological matter is smeared evenly over the internal wall in a thin coating by members 5 which ensures quick easy digestion by the enzymes rather than a previous situation where the biological matter was dispersed in localised "hills" and "valleys" and required longer periods of digestion. Ideally, such a device could be made sufficiently inexpensively so that it could be discarded after use, or at most discarded after a days use. For preference, the wiping member is injection moulded onto the end of the body which is also made of a polymer which has been extruded. The melting point of the portion to be injection moulded is ideally such as to cause a fusion with the extruded polymer during the injection moulding process, such that the two portions cannot be separated. The fins are spaced apart on the solid extruded core 6.

Spaced apart fins appear to more efficiently remove contamination than a single fin due to the rheology of the contaminant mixture.

Typically, the diameter of the lumen of an endoscope in the range 1 to 4.8 mm. It is preferred that the device according to the present invention has a cleaning member which is around 0.1 mm narrower, at its widest point, than the endoscope lumen. Given the expected tolerances in injection moulding, it is expected that the diameter would be within 0.1 mm of the theoretical diameter. However, for lumens of other diameter the size of the cleaning member can be varied as required. The cleaning or wiping member may be formed from one or more than one components.

Preferably, the body is composed of polypropylene, nylon, stainless steel spring tempered wire or the like.

As the inside of the endoscope lumen is usually made of polyurethane in the case of flexible endoscopes, and stainless steel in the case of rigid endoscopes, it is important that the cleaning member be selected from a material which will not score this inner surface of the lumen. Thus, desirably the cleaning member is formed from a material which is not as hard as the inside of the endoscope.

In a comparative study, a transparent lumen of similar dimension to the lumen of an endoscope is contaminated with a mucous which is of similar physical characteristics to those encountered in the normal use of the instrument. Repeated use of a brush of the kind now commonly employed was found to remove some of the contaminants but left a substantial quantity within the lumen. The remaining contaminants were very unevenly distributed both in the axially direction and in the circumferential direction. Digestion in a solution (eg epizyme rapid bath) required 6 to 12 minutes.

When apparatus according to the invention was used, the interior of the lumen was substantially wiped clean with a single pull through, leaving a thin film of contaminant remaining. The thin film was seen to be uniformly distributed both radially and longitudinally. Because the contaminants are uniformly distributed, the enzymatic cleaning solution was able to substantially digest the film within 2 to 3 minutes. In the case of the non-uniform distribution of the remaining contaminants of the prior brushing art, the digestion in areas where contamination is of maximum thickness will take very much longer to digest than the thin film and the overall time to obtain a satisfactory decontamination will be greatly lengthened.

Desirably, a plurality of spaced apart disk shaped fins are employed. These fins are radially extending in the form of either a disk or cone or they may be a succession of disks or cones graded in diameter. A fin may be of greater diametric dimension than that of the lumen and in that case will be resilient at least at its periphery. The fin may also be in the form of a spiral. At least one fin desirably extends circumferentially but a plurality of fin sectors extending over less than 360° at the circumference and angularly disposed so as to occlude each other may be employed, provided a homogeneous film results.

Fins extending in a circumferential direction at their outer periphery may have one or more space protrusions to maintain the cleaning member at a uniform circumferential spacing from the lumen wall.

Figure 3:
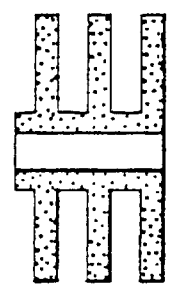
FIGS. 3–8 show alternative embodiments of the cleaning member of the present invention.

FIGS. 3–8 show other embodiments of the invention with regards to variations of the cleaning member 3. For example, FIG. 3 shows a cleaning member with the fins of equal size.

Figure 4:
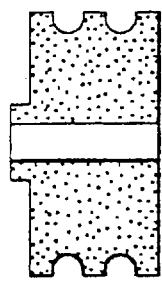
Figure 5:
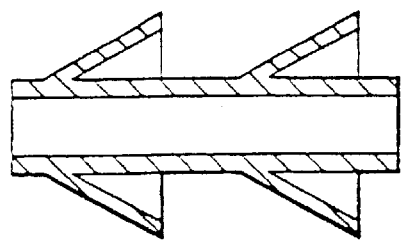
Figure 6:
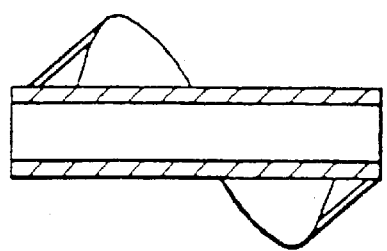
Figure 7:
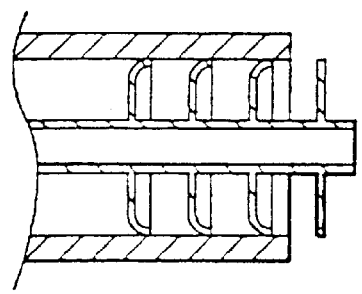
Figure 8:
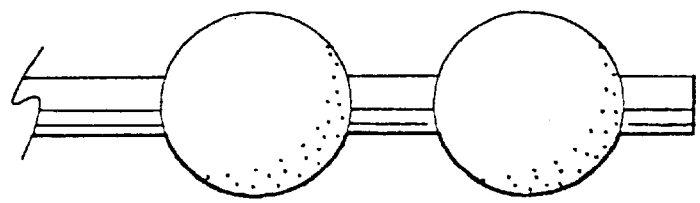

FIG. 4 shows a cleaning member formed of a single block with circumferential grooves. The fins do not have to be disposed at 90° to the body, for example FIG. 5 shows a series of cone shaped fins and FIG. 6 shows a spiral. FIG. 7 shows an embodiment of the invention wherein the fins are larger than the lumen but are resiliently biased at the edges. FIG. 8 shows a cleaning member wherein the wiping action is produced by a plurality of balls.

COMPARATIVE EXAMPLES

TEST METHOD FOR VALIDATING THE EFFICACY OF ENDOSCOPIC CLEANING DEVICE

The test described herein is derived from a variety of tests used worldwide, for example, British Standard Test Method BS2745.

TEST CONTAMINATION SAMPLE

In this example, a variety of materials representing the various classes of human secretions, mixed with bacterial spores at a known level, form the basis for the artificial contamination. The composition is similar to that described in the abovementioned British standard test. This contaminant in a known volume is used to contaminate the lumen to be cleaned. The test organism used is Bacillus subtilis variety globigii. This is an aerobic spore forming bacteria which is easy to cultivate and grows on nutrient broth and nutrient agar and is non-hazardous to laboratory personnel. The test organism is grown on a nutrient broth for two to three days at 37° C. The spores are harvested by centrifuging and washing four times in sterile distilled water. The final spore wash is heated to 80° C. for 15 minutes to kill any remaining vegetative cells. The yield of spores will be approximately $10^9$ spores/mil. This spore suspension is stored at 4° C. until required and is not retained for more than one week.

TEST CONTAMINATION MIXTURE

The following is used to prepare the artificial contaminant,

Beef-Steak=50 g,
Raw egg=50 g,
Boiled potato=50 g,
Hog Mucin=2 g,
Water to 500 ml.

The ingredients are dispersed in a blender for 10 minutes.

The spore suspension is then diluted to yield $10^9$ spores/ml. 1.0 ml of the spore suspension containing $10^9$ spores is mixed with 100 ml of the artificial contaminant. This serves as the test material.

INTRODUCTION OF CONTAMINANT 10 ml of the contaminant mixture is injected into the biopsy lumen of a colonoscope. Care is taken so that the contaminant mixture remains inside the biopsy lumen and is coated over the lumen wall by rotating the endoscope after the introduction of the contaminant.

PHYSICAL CLEAN USING PRIOR ART CLEANING BRUSH

The soiled endoscope is immersed in a water bath. A standard Pentax™ cleaning brush is introduced into the contaminated biopsy lumen and energetically brushed forwards and backwards for the whole length of the lumen for a period of 30 seconds.

The brush is removed and the endoscope is then removed from the bath, the water is allowed to drain and the endoscope is submerged in a known volume of an endoscopic cleaning solution (Epizyme Rapid) diluted according to instruction at a rate of 75:1 water to product. The bath is maintained in the temperature range 25–30° C.

A clean 50 ml syringe is used to ensure that the endoscope channel is filled with the cleaning solution. The instrument is allowed to stand for 5 minutes, whereupon the syringe is used to irrigate the channel five times with 50 ml taken from the bath on each occasion.

USE OF ENDOSCOPE CLEANING DEVICE ACCORDING TO THE PRESENT INVENTION

The soiled endoscope is immersed in a water bath. An endoscope cleaning device according to the present invention and as shown in FIG. 1 was introduced into the proximal end of the contaminated biopsy lumen and pulled from the proximal end through to the distal end once.

The device is removed and the endoscope is then removed from bath, the water allowed to drain, and the endoscope submerged in a known volume of endoscopic cleaning solution (epizyme rapid) diluted according to instructions at a rate of 75:1 water to product. The bath is maintained in the temperature range 25 to 30° C. A clean 50 ml syringe is used to ensure that the endoscope channel is filled with the cleaning solution. The instrument is allowed to stand for 5 minutes, whereupon the syringe is used to irrigate the channel five times with 50 ml taken from the bath on each occasion.

CONTROL

The contaminated endoscope is emersed without physical cleaning into a fresh endoscopic cleaning solution bath made up as described above and allowed to soak for 5 minutes as described and then irrigated as described above.

ENUMERATION OF BACTERIAL COUNT

The spore count is determined by taking a 50 ml sample from the cleaning bath after enidoscope removal and agitation of the bath. 1 ml of the sample is diluted to 9 ml with the nutrient broth and this sample further diluted 1 in 10 and up to 1 in 100,000.

1 ml of the above diluted samples are plated in duplicate in nutrient agar. The plates are allowed to solidify and are incubated at 37° C. for three days. The number of colonies were then determined for all samples and the colony counts converted to $\log_{10}$ for all the samples.

| SAMPLE | PROCEDURE | SPORES |
| --- | --- | --- |
| Control | No physical cleaning, 5 minute bath | 7.35 |
| Use of prior art cleaning brush | 30 second scrub, 5 minute bath | 4.89 |
| Use of embodiment of FIG. 1 | Single pull through 5 minute bath | 1.53 |

TIME TAKEN TO REACH THE SPORE COUNT IN THE RANGE OF LOG5 TO LOG6

| SAMPLE | TIME TAKEN |
| --- | --- |
| Control | 16 minutes |
| Prior Art Cleaning Brush | 10 minutes |
| Embodiment of FIG. 1 | 1 minute |

As will be understood by those skilled in the art based on the teaching hereof the invention may be embodied in other forms and may utilise other materials without departing from the concepts herein described.

The claims of the invention are as follows:

1. A method for cleaning a contaminated lumen of an endoscope comprising:
moving a wiping member having a diameter less than the diameter of the lumen axially through the lumen of an endoscope, the wiping member including a fully circumferential trailing wiping element, and wiping an internal wall of the lumen so that contaminants remaining after passage of the member are uniformly distributed on the internal wall of the lumen as a thin film; and
treating the thin film with a cleaning composition including at least one enzyme.

2. The method according to claim 1 wherein the thin film is substantially homogeneous in thickness in both a radial and longitudinal direction.

3. The method according to claim 1 including producing the thin film with a single pass of the wiping member through the lumen.

4. The method according to claim 1 including pulling the wiping member through the lumen with a flexible polymeric cable.

5. The method according to claim 1 further comprising disposing of the wiping member after use.

6. An apparatus for use in a method according to claim 1, said apparatus comprising a wiping member for passing axially through the lumen so that contamination remaining after passage of the member through the lumen is substantially uniformly distributed on the internal wall of the lumen as a thin film and wherein the wiping member has a smaller diameter than the lumen and includes a fully circumferential trailing wiping element.

7. The apparatus according to claim 6 wherein the wiping member is attachable to one of an elongate shaft and a cable.

8. The apparatus according to claim 6 wherein the wiping member is permanently attached to one of an elongate shaft and a cable.

9. The apparatus according to claim 8 wherein the elongate shaft and cable are flexible.

10. The apparatus according to claim 8 wherein the elongate shaft and cable are a polymeric material.

11. The apparatus according to claim 6 wherein the wiping member includes at least one radially extending fin as a wiping element.

12. The apparatus according to claim 6 wherein the wiping member includes a plurality of radially extending fins as wiping elements.

13. The apparatus according to claim 6 wherein the wiping member includes a disk shaped wiping element.

14. The apparatus according to claim 6 wherein the wiping member includes a cylindrical wiping element.

15. The apparatus according to claim 6 wherein the wiping member includes a spherical wiping element.

16. The apparatus according to claim 6 wherein the wiping member includes a spiral wiping element.

17. The apparatus according to claim 6 wherein the wiping member includes a conical or frustoconical wiping element.

18. The apparatus according to claim 6 wherein the wiping member has a hollow core.

19. The apparatus according to claim 6 wherein the wiping member has a solid core.

20. The apparatus according to claim 6 wherein the wiping member includes a plurality of wiping elements graded in diameter.

21. The apparatus according to claim 6 wherein the wiping member includes at least one partially circumferential wiping element and a fully circumferential trailing wiping clement.

22. The apparatus according to claim 6 wherein the wiping member includes a non-absorbent material.

23. The apparatus according to claim 6 wherein the wiping member includes an elastomeric material.

24. The apparatus according to claim 6 further including a rounded end proximal the wiping member.

25. The apparatus according to claim 6 including a polymeric shaft and the wiping member is moulded onto the shaft.

26. The apparatus according to claim 6 wherein said apparatus is disposable.

27. The method for manufacture of an endoscope cleaning apparatus as defined in claim 7 comprising moulding a wiping member comprising at least one radially directed fin in situ on a polymeric elongated shaft or cable.

28. The method according to claim 27 wherein the polymeric shaft or cable is one of nylon and polypropylene.

29. The method according to claim 27 wherein the wiping member is moulded onto the shaft.

30. The method according to claim 29 including injection moulding the wiping member onto the shaft.

31. The method according to claim 27 wherein the wiping member and shaft include complementary engageable threads.

32. The method according to claim 27 including press forming the wiping member onto the shaft.

33. The method according to claim 27 including moulding the wiping member from at least two components.

34. The method according to claim 27 including fusing the wiping member to the shaft.

35. The kit including apparatus according to claim 6 and an enzyme cleaning composition, said wiping member being selected to provide a residue thickness on the internal wall of the lumen of the endoscope and said cleaning composition being selected for digesting the residue within a predetermined time.

36. The method according to claim 1 wherein the thin film is substantially homogenous in thickness in both a radial and longitudinal direction.

37. An apparatus for use in cleaning a contaminated lumen of an endoscope, said apparatus being moulded from polymeric materials and comprising a fully circumferential wiping member with a smaller diameter than the lumen attached to a cable for passing axially through a lumen of an endoscope with a clearance, whereby contamination remaining after passage of the member through the lumen is substantially uniformly distributed on the lumen as a thin film.

* * * * *